United States Patent
Buchwald et al.

(10) Patent No.: US 9,909,861 B2
(45) Date of Patent: Mar. 6, 2018

(54) METHOD AND DEVICE FOR DETECTING THE EDGE PROFILE OF BOTTLES OR SIMILAR CONTAINERS

(75) Inventors: Carsten Buchwald, Bad Breisig (DE); Wolfgang Schorn, Hönningen (DE)

(73) Assignee: KHS GmbH, Dortmund (DE)

( * ) Notice: Subject to any disclaimer, the term of this patent is extended or adjusted under 35 U.S.C. 154(b) by 2011 days.

(21) Appl. No.: 12/995,424

(22) PCT Filed: May 19, 2009

(86) PCT No.: PCT/EP2009/003537
§ 371 (c)(1),
(2), (4) Date: Mar. 7, 2011

(87) PCT Pub. No.: WO2009/156027
PCT Pub. Date: Dec. 30, 2009

(65) Prior Publication Data
US 2011/0149065 A1    Jun. 23, 2011

(30) Foreign Application Priority Data
Jun. 25, 2008  (DE) .......... 10 2008 029 855

(51) Int. Cl.
*H04N 7/18* (2006.01)
*G01B 11/24* (2006.01)
*B67C 3/00* (2006.01)
*G01N 21/90* (2006.01)

(52) U.S. Cl.
CPC .......... *G01B 11/2433* (2013.01); *B67C 3/007* (2013.01); *G01N 21/9036* (2013.01)

(58) Field of Classification Search
CPC .... G01N 21/90; G01N 21/88; G01N 21/9036; B67C 3/007; G01B 11/2433

USPC ............................................ 348/127, E7.085
See application file for complete search history.

(56) References Cited

U.S. PATENT DOCUMENTS

| 5,280,170 | A | * | 1/1994 | Baldwin .................... 250/223 B |
| 5,917,602 | A | * | 6/1999 | Bonewitz et al. ............ 356/614 |
| 2002/0145103 | A1 | | 10/2002 | Bernardini |
| 2005/0135706 | A1 | | 6/2005 | Sengupta et al. |

FOREIGN PATENT DOCUMENTS

| DE | 195 12 133 | 10/1995 |
| DE |  19625055 | 4/1997 |
| DE | 200 05 283 | 7/2000 |
| EP |  0 298 588 | 1/1989 |

(Continued)

OTHER PUBLICATIONS

Gottfried Schröder: "5.2 Bildshirme" in; Technische Optik: Grudlagen and Anwendungen, 1990, Vogel, Würzburg, Seiten 104-106.

*Primary Examiner* — William C Vaughn, Jr.
*Assistant Examiner* — Naod Belai
(74) *Attorney, Agent, or Firm* — Occhiuti & Rohlicek LLP

(57) ABSTRACT

The invention relates to a method and device for detecting the edge profile of bottles or similar containers that are moved past a measuring and/or receiving region of a measuring and/or receiving system, using at least one optoelectric receiver on one side of the measuring and/or receiving region and using at least one light-emitting device on the side located opposite of the receiver in the measuring and/or receiving region.

20 Claims, 3 Drawing Sheets

(56) References Cited

FOREIGN PATENT DOCUMENTS

| EP | 298588 A1 * | 1/1989 | ............. G01B 11/24 |
|----|----|----|----|
| EP | 0 896 244 | 2/1999 | |
| EP | 1 176 417 | 1/2002 | |
| JP | 09 089805 | 4/1997 | |
| WO | 97/12200 | 4/1997 | |
| WO | 97/21072 | 6/1997 | |
| WO | 2008/027569 | 3/2008 | |

* cited by examiner

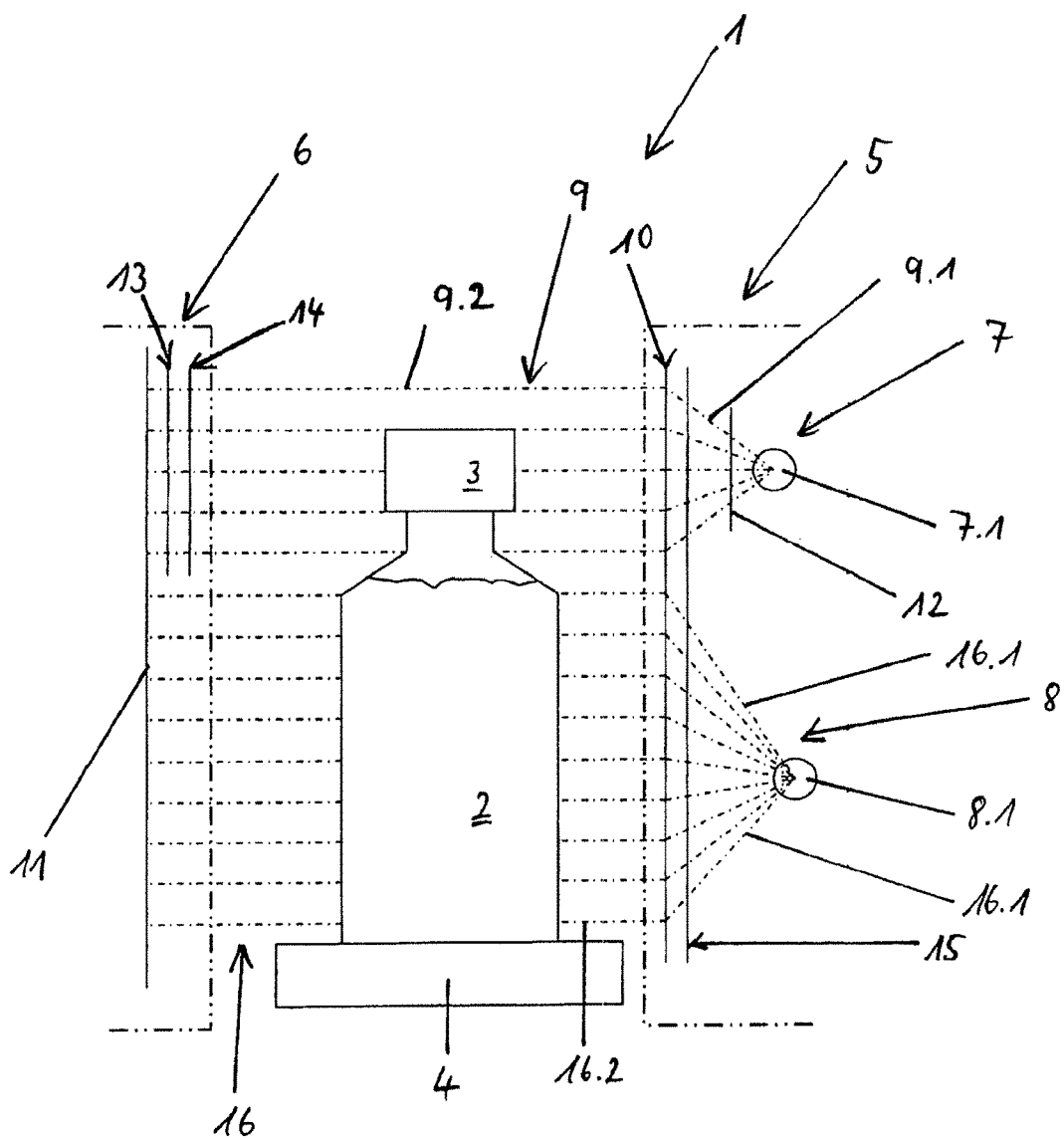

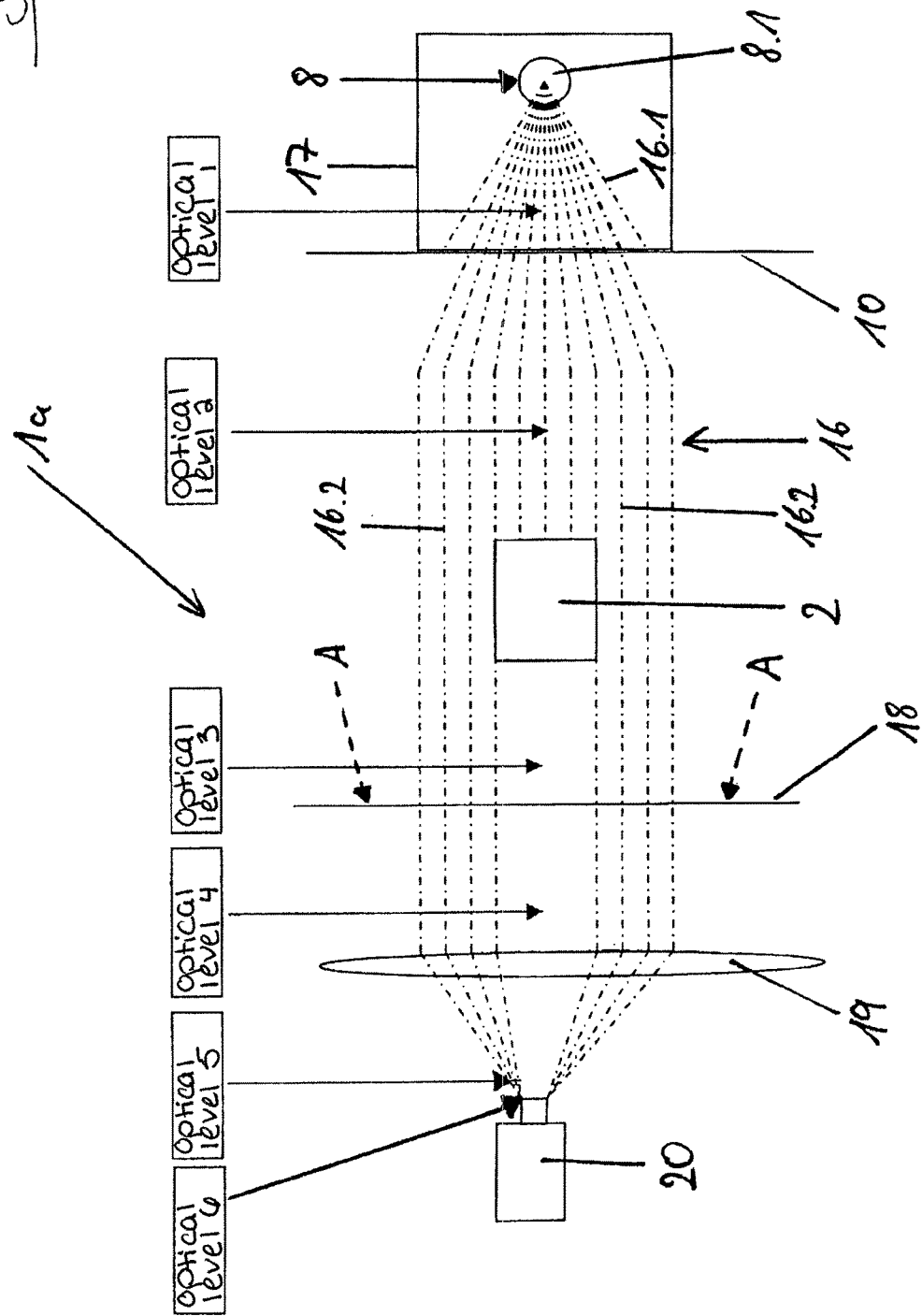

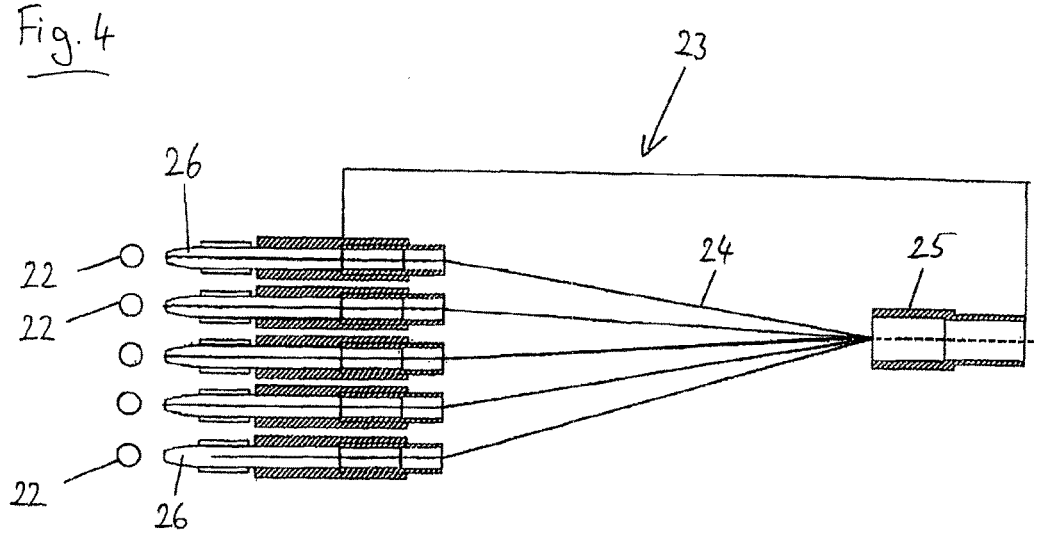
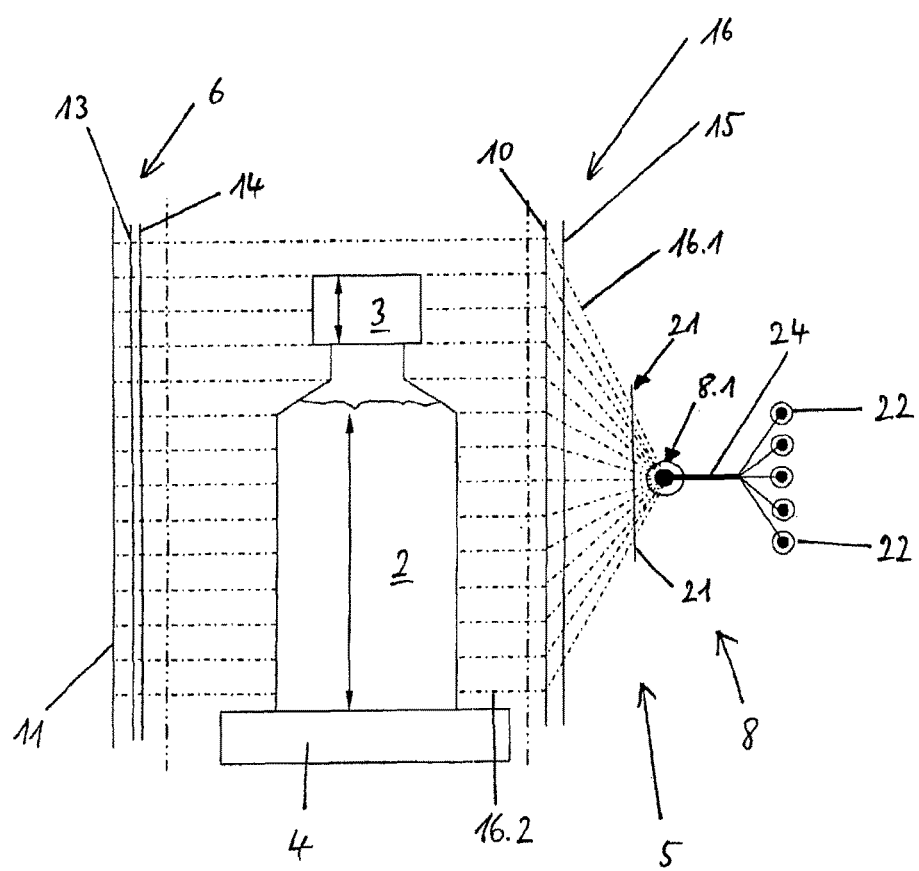

METHOD AND DEVICE FOR DETECTING THE EDGE PROFILE OF BOTTLES OR SIMILAR CONTAINERS

CROSS-REFERENCE TO RELATED APPLICATIONS

This application is the National Stage of International Application No. PCT/EP2009/003537, filed on May 19, 2009, which claims the benefit of German Application Serial No. 10 2008 029 855.7, filed on Jun. 25, 2008, the contents of both of the foregoing applications are hereby incorporated by reference in their entirety.

FIELD OF INVENTION

The invention relates to image processing, and in particular, to detection of an edge.

BACKGROUND

Methods and devices or imaging or measuring systems for imaging bottles or similar containers, in particular also for detecting edge profiles of containers are known. In such systems, containers move past a recording or measuring region of the imaging or measuring system on a conveyor or conveyor belt. Using a CCD camera with an entocentric lens and a luminescent screen, such systems carry out varied measuring methods through trans-illumination or silhouette procedures.

A non-distortion free beam path afflicts these systems with serious imaging errors. These imaging errors can be reduced to a passable level using special lenses, for example telecentric lenses. But telecentric lenses are extremely expensive and also have a greatly reduced depth of focus. When such lenses are used, it becomes necessary to precisely position containers within a measuring-and-recording region of the measuring system.

SUMMARY

It is an object of the invention to provide a method that makes possible distortion-free or substantially distortion-free detection of edge profiles of bottles or of similar containers, and to reduce the construction costs of the device used as the measuring and imaging system.

In the case of one embodiment of the invention, a line imaging means or a line camera generates chronological line-shaped or strip-shaped recordings of each container moved past the measuring or recording region. From these recordings, an edge profile of the relevant bottle is then assembled. The line imaging means, in this case, is distortion-free and yields recordings without color or gray content.

Where a line imaging means or a line camera is used, line images are generated, for example, parallel to a container axis, e.g. parallel to a vertical container axis. It is possible to adapt the resolution in the generated edge profile in the container axis to the respective requirements by adjusting the resolution of the line imaging means or of the line camera, in a direction that is transverse relative to the axis of the line images, i.e. e.g. transverse relative to the container axis. This can be carried out by adjusting the number of recordings per unit time.

The individual line images are generated, for example, by corresponding actuation of the line imaging means or of the line camera and/or by corresponding actuation of the light-transmitting device. It is possible to use the edge profile created in each case from the containers for the most varied control and monitoring purposes.

In the case of a preferred embodiment of the invention, a parallel silhouette of the respective container is preferably realized on a luminescent screen or display screen with the parallel light of the at least one light-transmitting device. The screen is preferably realized such that, on its side facing the at least one optoelectronic receiver (e.g. the line imaging means, the line camera or a CCD camera), there is an image or a silhouette of the respective container, which is generated exclusively by the parallel light or the parallel light beams of the light. This means that a distortion-free and sharp-edged silhouette is obtained on the side of the luminescent screen or display screen facing the at least one optoelectronic receiver. In particular, distortions caused by non-parallel light beams and extraneous light hitting the luminescent screen or display screen in an inclined manner are avoided.

In the simplest scenario the display screen, in this case, comprises a flat material or a film that is transparent only or substantially only to vertically incident light. An example of such a flat material or film includes a polarizing filter foil or directional filter foil.

An advantage of the invention is that it provides a simplified, cost-efficient design of the device or of the measuring and/or imaging system.

Another advantage arises from the possibility of using entocentric lenses for the optoelectronic receiver or the line camera, the line imaging means or the CCD camera that is used. Such lenses are usual in the trade and are commercially available at a good price.

Yet another advantage arises from the possibility of extremely short exposure times by focusing the light or light beam in a targeted manner. This improves independent from, among other things, extraneous light.

Other advantages include the ability to achieve distortion-free imaging, the ability to achieve homogenous light density even when only weak light sources are used, and the high depth of focus, in particular even when using an optoelectronic receiver or a line imaging means, a line camera or a CCD camera with an entocentric lens.

In one aspect, the invention features a method for detecting edge profiles of containers moved past a measuring and/or recording region of a measuring and/or recording system using an optoelectronic receiver on one side of the measuring and/or recording region and a light-transmitting device located opposite the optoelectronic receiver in the measuring and/or recording region. Such a method includes using the light-transmitting device, generating a parallel or substantially parallel light, directing the light onto a container moved through the measuring and/or recording region, using an optoelectronic receiver, generating chronological line images of the container, and forming the edge profile of the container from the line images.

In some practices, the optoelectronic receiver comprises line imaging means. Such practices further include using the parallel light of the light-transmitting device, generating an image on a display screen, and using the line imaging means, generating the line images from the image on the display screen.

In another aspect, the invention features a method for detecting the edge profile of containers moved past a measuring and/or recording region of a measuring and/or recording system by using an optoelectronic receiver on one side of the measuring and/or recording region and a light-transmitting device located opposite the receiver in the measuring and/or recording region. Such a method includes using the light-transmitting device to generate a parallel or substantially parallel light, directing the light onto a container moved through the measuring and/or recording region, and using the parallel light of the light-transmitting device, generating an image of the container on a display screen, using one of the optoelectronic receiver and an optoelectronic camera, recording the image.

In some practices, recording the image comprises recording without color and gray scale values or equivalently, in the absence of color and gray scale values.

In other practices, using the light-transmitting device to generate light comprises delivering a light having a spectrum and modifying the spectrum of the light. Among these practices are thise that include detecting an edge profile of the container by modifying, at least once in a synchronous manner, either the spectral region of the light of the light-transmitting device, the filters located in the path of the light, a transmission characteristic of one of the filters, or any combination of the foregoing.

Other practices include providing a display screen having a transmission characteristic such that the display screen is transparent only to a light incident from a predetermined direction.

In other practices, generating an image of the container comprises generating a silhouette of the container.

Also among the practices of the invention are those in which generating line images of the container comprises generating line images with lines having a width of one pixel.

In another aspect, the invention features an apparatus comprising a device for detecting the edge profile of containers. Such a device includes at least one optoelectronic receiver on a side of a measuring and/or recording region, through which the containers are moved on a conveyor, the optoelectronic receiver including line imaging means for recording line images, at least one light-transmitting device located opposite the receiver on the measuring and/or recording region, the at least one light-transmitting device being configured for generating substantially parallel light that penetrates the measuring and/or recording region and is directed onto the at least one receiver.

In some embodiments, the optoelectronic receiver has, associated therewith, a display screen on which an image of the container is generated using the parallel light generated by the one light-transmitting device. In these embodiments, the line imaging means is located in a beam path following the display screen.

Yet another aspect of the invention features an apparatus having a device for detecting the edge profiles of containers. Such a device includes at least one optoelectronic receiver on one side of a measuring and/or recording region, through which the containers are moved on a conveyor, at least one light-transmitting device located opposite the receiver at the measuring and/or recording region, the at least one light-transmitting device being configured for generating substantially parallel light that penetrates the measuring and/or recording region and is directed onto the optoelectronic receiver, wherein the at least one optoelectronic receiver has associated therewith a display screen on which an image of a container is generated by using the parallel light generated by the at least one light-transmitting device, and wherein the at least one optoelectronic receiver comprises a camera located in the path of the beam following the display screen.

Some embodiments also have an additional measuring and/or recording region through which containers are moved in a conveyor, and at least one of an additional light-transmitting device configured for generating substantially parallel light through the additional measuring and/or recording region and an additional optoelectronic receiver on one the additional measuring and/or recording region.

In other embodiments, the at least one light-transmitting device comprises at least one of at least one substantially punctiform light source and at least one lens system for generating the parallel light, and at least one light source for delivering a light that has a modified spectrum.

Other embodiments include optical filters located in a beam path of the light generated by the at least one light-transmitting device, the optical characteristics of the optical filters being adaptable to modify the light spectrum of the light-transmitting device.

In some embodiments, the display screen has a transmission characteristic such that the display screen is only transparent to light incident from a pre-determined direction.

In other embodiments, the light source comprises a plurality of individual light sources, and a lens for pooling the light provided by the individual light sources to form a punctiform light source.

In yet other embodiments, the optoelectronic receiver comprises a line camera configured to receive light directly, without the light having passed through a lens.

Embodiments also include those in which the camera comprises a line camera, and those in which the camera comprises a CCD camera.

Further developments, advantages, and application possibilities of the invention will be apparent from both the following description of exemplary embodiments and from the figures. In this case, all described and/or graphically represented features are in principle objects of the invention, either individually or in arbitrary combination, irrespective of their summary in the claims or their dependency. The content of the claims is also made a component of the description.

BRIEF DESCRIPTION OF THE FIGURES

The invention is described in more detail below by way of FIGS. 1-4, each of which show a simplified schematic representation of optoelectronic imaging or measuring devices according to the invention or of a device for coupling a plurality of individual light sources into one common focal point.

DETAILED DESCRIPTION

A first device 1, shown in FIG. 1 is used, among other things, for optoelectronically detecting or for recording the edge profile of a container 2 that is filled with a liquid product and closed by a closure 3. The first device 1 is used, for example, for determining, using the edge profile, the actual volume of the container 2. Based on this measured actual volume, it is possible to use a liquid-level checking means or a fill-level checking means to determine or check whether the measured fill level actually corresponds to required volume.

In addition, the first device 1 is also suitable, among other things, for checking a container 2 to see if it has a closure 3 and/or to confirm that the closure is correctly applied.

The first device 1 includes a conveyor belt 4 for moving containers 2, such as bottles, for example, PET bottles that are standing upright, i.e. with their container bottoms on a conveyor belt 4. The device further comprises a measuring and/or recording system. The measuring and/or recording system has a transmitting side 5 on one longitudinal side of the conveyor belt 4 and a receiving side 6 along another longitudinal side of the conveyor belt 4 opposite the transmitting side 5. Neither the transmitting side 5 nor the receiving side 6 are entrained with the conveyor belt 4.

The transmitting side 5 has first and second light-transmitting devices 7, 8 one above the other in the vertical direction. The first light-transmitting device 7 is formed by a first light source 7.1 with a predetermined light spectrum. The second light-transmitting device 8 is formed by a second light source 8.1 that is suitable for delivering light in various spectra. Both the first light source 7.1 and the second light source 8.2 are punctiform or substantially punctiform.

The second light source 8.1 is formed by a plurality of individual light sources with associated lenses for trapping the light. In one embodiment, the first light source 7.1 and the individual light sources that form the second light source 8.1 have one or more LEDs.

The light 9 from the first light source 7.1 includes a diverging light portion 9.1, radiated initially in a diverging manner from the light source 7.1 (light bundle made up of diverging light beams). An optical lens system 10 that functions as a collimator transforms this diverging light portion 9.1 into horizontal, parallel light portion 9.2 made up of parallel light beams that are incident on the receiving side 6.

At the receiving side 6, the container 2 blocks part of the parallel light portion 9.2 thus causing a silhouette or shadow profile of the container. The optoelectronic receiver 11 detects this in the region of the closure 3 and outputs an edge profile, as shown in FIG. 1.

The optoelectronic receiver 11 includes a line camera with entocentric lenses. The line camera obtains a plurality of chronological recordings of the top region. Each recording is a vertically-oriented line image. In some embodiments, the line image is only one pixel wide.

As the container 2 moves through the device, the line images show its closure 3. To obtain the edge profile of a container 2 in the vicinity of its closure 3, one assembles the line images without color or grey scale values, taking into consideration the speed of conveyance of the conveyor belt 4. For this purpose, the light-transmitting device 7 is located such that the containers 2, with their closures 3, move through the parallel light portion 9.2.

A first filter 12 between the light source 7.1 and the lens system 10 in the path of the light 9 selects an optimum part of the spectrum for detecting the edge profile. The first filter 12 selects an optimum part spectrum of the light 9 supplied by the light source 7.1, taking ambient light into consideration. Preferably, the first filter 12 is a replaceable filter.

Corresponding second and third filters 13 and 14 are provided on the receiving side 6 in front of the optoelectronic receiver 11. A field stop 15 with a stop opening is additionally located in the beam path between the first filter 12 and the lens system 10. The field stop 15 defines the light of the light source 7.1 so as to detect the region near the closure 5 of each container 2 by way of the parallel light 9.2 emerging from the lens system 10.

The light 16 of the light source 8.1 is shown generally in FIG. 1. The light 16 includes a diverging light portion 16.1 that is radiated initially in a diverging manner by the light source 8.1. The optical lens system 10, operating as a collimator, converts this diverging light portion 16.1 into a parallel light portion 16.2 oriented vertically relative to the direction of transport of the conveyor belt 4. The parallel light portion 16.2 is incident on the receiving side 6.

On the receiving side 6, the parallel light portion 16.2 generates an edge profile of a container 2 as a parallel silhouette or shadow profile. The optoelectronic receiver 11 detects this edge profile in the region below the closure 3.

The detection is carried out by a plurality of chronological recordings, each of which is a line image of the container region below the closure 3. The line image is that of a line oriented in the vertical direction and, for example, only one pixel wide. The edge profile below the closure 3 is then generated by assembling or putting together these line images without gray scale or color values, and taking the speed of conveyance of the conveyor belt 4 into consideration. For this purpose, the light source 8.1 is located below or at a level below the light source 7.1 such that the containers 2 are moved through the parallel light portion 16.2 with their container region below the closures 3.

Changeable filters (not shown), corresponding to the first and second filters 12 and 13 are provided in front of the optoelectronic receiver 11, also in the beam path of the parallel light portion 16.2. The changeable filters have transmission characteristics that modify the spectrum of the light 16 transmitted by the light source 8.1 in such a way that the receiver-side filters are adapted, modified or changed synchronously with the change in the light spectrum of the light source 8.1. As a result, it is possible to generate line images of the container 2 with different light spectra for further improving the detection of the edge profile of the containers 2 by modifying the spectrum of light from the light source 8.1 and the changeable filters on the receiving side in a synchronized manner.

The opening in the field stop 15 or the stop opening provided at that location is realized such that the containers 2 are detected substantially only in a region below the closure 3 by way of the parallel light portion 16.2.

In principle, all optical lenses or lens systems that are suitable as collimators or for converting a diverging light beam into parallel light are suitable as lens system 10.

It has been assumed above that the optoelectronic receiver 11 has at least one line camera with a cost-efficient entocentric lens and that line images of the shadow contour of the containers 2 are taken with this camera without color or grey scale values and joined together to generate the container contours in the region of the closure and below the closure. In principle, however, it is also possible to provide another optoelectronic receiver 11, e.g. a CCD camera with an entocentric lens, in place of a line camera.

In the case of a preferred variant, the line camera does not have any lens. It only has the actual recording means.

In addition, it has also been assumed above for reasons of simpler representation that the lens system 10 and the field stop 15 are provided together for both light-transmitting devices 7, 8. However, in some embodiments, independent lens systems 10 and/or field stops 15 are provided for the light-transmitting devices 7, 8.

FIG. 2 shows a simplified representation and top view of a second device 1a that differs from the first device 1 in a few details but that uses the same measuring and imaging principle. FIG. 2 represents one of the two light-transmitting devices, for example the light-transmitting device 8 with the punctiform or substantially punctiform light source 8.1, once again formed by one or several LEDs, the light source being located in a lens barrel 17 with a mechanical stop and radiating its light 16 initially as a diverging light portion 9.1, i.e. a light bundle made of diverging light beams. The diverging light portion 16.1 is converted into the parallel light portion 16.2, i.e. a light bundle made of parallel light beams, at the lens system 10, which operates as a collimator. In some embodiments, the lens system 10 and is formed by a Fresnel lens. A conveyor 4 moves the measured object, i.e. the container 2, through the parallel light portion 16.2.

The light source 8.1, the lens barrel 17 and the lens system 10 are once again part of the transmitting side 5 of the measuring and/or imaging system. A luminescent screen or display screen 18 is provided on the receiving side 6 situated opposite the transmitting side 5. The parallel silhouette generated by the measured object or by the container 2 being imaged is formed in a distortion-free manner with the parallel light portion 16.2 on the luminescent screen or display screen. By means of an optical system 19, for example in the form of a plano-convex lens, following the display screen in the path of the beam, and by means of the lenses, e.g. the entocentric lens of an optoelectronic sensor, for example, a line camera or a CCD camera, the silhouette generated on the display screen 18 is recorded. This is effected once again preferably without color or gray scale content, e.g. in the form of line images, from which the edge profile of the measuring object or container 2 is then put together.

The display screen 18 is preferably designed such that the screen only allows passage of the parallel light portion 16.2, i.e. the vertically incident light, and not inclined incident light, in particular not inclined incident ambient light or extraneous light, which is indicated by the arrows A in FIG. 2. This considerably improves the distortion-free, sharp representation of the edge profile on the display screen 18. In particular, distortions caused by extraneous light are effectively avoided. A polarization filter foil or a directional filter foil is suitable, for example, as a material for the display screen 18.

The lens system 10 or the lenses forming the lens system and operating as a collimator are provided separately in each case for the light source 7.1 and 7.2 in order, in this manner, through the arrangement of the light sources at the focal point, to convert the diverging light portion 9.1, 16.1 into the parallel light portions 9.2, 16.2.

The second, and third filters 13, 14 and the field stop 15 can vary depending on the design and/or application. It is also possible to dispense with one or more of the filters.

With reference to FIG. 2, the optical design of the measuring and imaging system of the second device 1a and its method of operation can be described in a summarizing manner as follows:

The punctiform light source 8.1 generates a luminous surface with an entocentric development;

The lens barrel 17 with a mechanical stop centers the punctiform light source 8.1 (optical level 1). The lens system 10 (e.g. Fresnel lens) then generates the parallel light portion 16.2 (optical level 2) from the diverging light portion 16.1. The object to be measured, for example the container 2, casts a distortion-free shadow onto the display screen 18 (optical level 3). The image on the display screen 18 (optical level 4) is then focused via the lens system 19 (optical level 5) and is recorded by the line camera or CCD camera (optical level 6).

Once again, various modifications are also possible to the second device 1a. Thus, for example, the lens system 19, i.e. the plano-convex lens is only necessary when using a CCD camera 20 as optoelectronic receiver. When using a line imaging means as the optoelectronic receiver 20, no plano-convex lens 19 is required. The first, second, and third filters 12, 13 and 14 can vary depending on the design and/or application, and/or can be completely or partially omitted.

In a simplified schematic representation similar to FIG. 1, FIG. 3 shows a third device 1b, which differs from the first device 1 in some details, but basically relies on the same measuring and imaging principle. The essential difference between the third device 1b and the first device 1 is that only a single light-transmitting device is provided on the transmitting side 5. namely, for example, the light-transmitting device given the reference 8 in FIG. 3 with the light source 8.1, which is located in the focal point of the lens system 10 (operating as a collimator) with field stop 15 such that the diverging light portion 16.1 is once again converted into the parallel or substantially parallel light portion 16.2, in such a manner that by way of the parallel light portion 16.2, the respective container 2 is detected over its entire height, i.e. including the container closure 3. In addition, a filter 21 corresponding to the first filter 12 is provided between the field stop 15 and the light source 8.1.

The receiving side 6 is realized in an identical or similar manner to the receiving side 6 of the measuring device 1, for example once again with the second and third filters 13 and 14 located in the beam path of the parallel light portion 16.2 and the optoelectronic receiver 11 connected downstream.

As is also represented in FIG. 3, the light source 8.1 is formed by a plurality of light-transmitting elements or individual light sources 22. The light sources 22 can be LEDs. In some embodiments, some or all of the LEDs are individually actuatable. This allows one to increase light intensity by turning on more of the of the individual light sources 22 and to decrease it by turning off individual light sources 22. Additionally, if the light sources 22 have different spectra, is possible to modify the spectrum of the light delivered by the light source 8.1 by switching on individual light sources 22 with the desired light spectrum and switching off those with an undesired light spectrum, for example to optimize the respective imaging and/or measuring procedure. To achieve this, there are embodiments in which the individual light sources 22 form, for example, groups of individual light sources 22, each with a different light spectrum, each group having at least one individual light source 22, and preferably several individual light sources.

Modifications similar to those discussed in the first and second devices can also be made to the third device 1b. Thus, the filters 13, 14 and 21 can vary depending on the design and/or application, or they can be completely or partially omitted. In addition, the lens system 10 that operates as a collimator can also comprise one or more lenses.

In a very schematic representation, FIG. 4 shows an optical arrangement, with which the individual light sources 22 are pooled together to form the light source 8.1 located in the focal point of the optical lens system 10. The optical arrangement, in the case of the embodiment represented, essentially comprises an optical fiber 23 with a plurality of optical wave guides 24, having light-transmitting ends combined together in an end sleeve 25 forming a bundle that becomes the light source 8.1. At the end that is remote from the end sleeve 25, each optical wave guide 24 has a connection 26, for example, a fiber optic head, for coupling-in light from the relevant individual light source 22. The fiber optic head makes it possible, in particular, to couple-in light with different wavelengths or even to select such in order to fulfill special inspection tasks. For example, light in the infrared range can be coupled into the fiber.

In order to combine light from a plurality of individual light sources 22 to form a light source 7.1, 8.1 located at the focal point of the lens system 10 or to couple light from a plurality of individual light sources 22 into the focal point of the lens system 10, other optical devices can be used in place of the optical fiber 23. For example, optical systems with prisms or optical elements that operate in a prism-like manner can also be used.

The punctiform light source 7.1 of the measuring device 1 is also realized, for example, in an identical manner as the light source 8.1, if the light source 7.1 also comprises a plurality of individual light sources, for example a plurality of LEDs.

The invention has been described above by way of exemplary embodiments. It is obvious that changes and conversions are possible without in any way departing from the inventive concept underlying the invention.

The invention claimed is:

1. A method for detecting edge profiles of containers moved past a measuring and/or recording region of a measuring and/or recording system using at least one optoelectric receiver on one side of the measuring and/or recording region and at least one light-transmitting device located opposite the optoelectric receiver in the measuring and/or recording region, said method comprising using the at least one light-transmitting device, generating a parallel or substantially parallel light, directing said light onto a container moved through the measuring and/or recording region, using at least one optoelectric receiver, generating chronological line images of the container, and forming the edge profile of the container from the line images, wherein the at least one optoelectric receiver comprises line imaging means, wherein said method further comprises using the parallel light of the at least one light-transmitting device, generating an image on a display screen, and using the line imaging means, generating the line images from the image on the display screen.

2. The method of claim 1, wherein generating an image of the container comprises generating a silhouette of the container.

3. The method of claim 1, wherein generating line images of the container comprises generating line images with lines having a width of one pixel.

4. A method for detecting the edge profile of containers moved past a measuring and/or recording region of a measuring and/or recording system by using at least one optoelectric receiver on one side of the measuring and/or recording region and at least one light-transmitting device located opposite the receiver in the measuring and/or recording region, said method comprising using the at least one light-transmitting device to generate a parallel or substantially parallel light, directing said light onto a container moved through the measuring and/or recording region, and using the parallel light of the at least one light-transmitting device, generating an image of the container on a display screen, using one of the optoelectric receiver and an optoelectric camera, recording said image, wherein using the at least one light-transmitting device to generate light comprises delivering a light having a spectrum and modifying the spectrum of the light.

5. A method for detecting the edge profile of containers moved past a measuring and/or recording region of a measuring and/or recording system by using at least one optoelectric receiver on one side of the measuring and/or recording region and at least one light-transmitting device located opposite the receiver in the measuring and/or recording region, said method comprising using the at least one light-transmitting device to generate a parallel or substantially parallel light, directing said light onto a container moved through the measuring and/or recording region, and using the parallel light of the at least one light-transmitting device, generating an image of the container on a display screen, using one of the optoelectric receiver and an optoelectric camera, recording said image, said method further comprising detecting an edge profile of the container, wherein detecting the edge profile comprises modifying, at least once in a synchronous manner, at least one of the spectral region of the light of the at least one light-transmitting device, filters located in the path of the light, and a transmission characteristic of one of said filters.

6. A method for detecting the edge profile of containers moved past a measuring and/or recording region of a measuring and/or recording system by using at least one optoelectric receiver on one side of the measuring and/or recording region and at least one light-transmitting device located opposite the receiver in the measuring and/or recording region, said method comprising using the at least one light-transmitting device to generate a parallel or substantially parallel light, directing said light onto a container moved through the measuring and/or recording region, and using the parallel light of the at least one light-transmitting device, generating an image of the container on a display screen, using one of the optoelectric receiver and an optoelectric camera, recording said image, said method further comprising providing a display screen having a transmission characteristic such that said display screen is transparent only to a light incident from a predetermined direction.

7. The method of claim 6, wherein recording said image comprises recording without color and gray scale values.

8. A device for detecting the edge profile of containers, said device comprising at least one optoelectric receiver on a side of a measuring and/or recording region, through which the containers are moved on a conveyor, the at least one optoelectric receiver including line imaging means for recording line images, at least one light-transmitting device located opposite the receiver on the measuring and/or recording region the at least one light-transmitting device being configured for generating substantially parallel light that penetrates the measuring and/or recording region and is directed onto the at least one receiver, wherein the at least one optoelectric receiver has associated therewith a display screen on which an image of the container is generated using the parallel light generated by the at least one light-transmitting device, and wherein the line imaging means is located in a beam path following the display screen.

9. A device for detecting the edge profiles of containers, said device comprising: at least one optoelectric receiver on one side of a measuring and/or recording region, through which the containers are moved on a conveyor, at least one light-transmitting device located opposite the receiver at the measuring and/or recording region, the at least one light-transmitting device being configured for generating substantially parallel light that penetrates the measuring and/or recording region and is directed onto the optoelectric receiver, wherein the at least one optoelectric receiver has associated therewith a display screen on which an image of a container is generated by using the parallel light generated by the at least one light-transmitting device, and wherein the at least one optoelectric receiver comprises a camera located in the path of the beam following the display screen, said device further comprising optical filters located in a beam path of the light generated by the at least one light-transmitting device, the optical characteristics of said optical filters being adaptable to modify the light spectrum of the light-transmitting device.

10. The device according to claim 9, further comprising: an additional measuring and/or recording region through which containers are moved in a conveyor, and at least one of an additional light-transmitting device configured for generating substantially parallel light through said additional measuring and/or recording region and an additional optoelectric receiver on one said additional measuring and/or recording region.

11. The device according to claim 9, wherein the at least one light-transmitting device comprises at least one of at least one substantially punctiform light source and at least one lens system for generating the parallel light, and at least one light source for delivering a light that has a modified spectrum.

12. The device according to claim 9, wherein the display screen has a transmission characteristic such that said display screen is only transparent to light incident from a pre-determined direction.

13. The device according to claim 9, wherein the at least one light source comprises a plurality of individual light sources, and a lens for pooling the light provided by the individual light sources to form a punctiform light source.

14. The device of claim 9, wherein the camera comprises a line camera.

15. The device of claim 9, wherein the camera comprises a CCD camera.

16. A device for detecting the edge profiles of containers, said device comprising: at least one optoelectric receiver on one side of a measuring and/or recording region, through which the containers are moved on a conveyor, at least one light-transmitting device located opposite the receiver at the measuring and/or recording region, the at least one light-transmitting device being configured for generating substantially parallel light that penetrates the measuring and/or recording region and is directed onto the optoelectric receiver, wherein the at least one optoelectric receiver has associated therewith a display screen on which an image of a container is generated by using the parallel light generated by the at least one light-transmitting device, and wherein the at least one optoelectric receiver comprises a camera located in the path of the beam following the display screen, said device, wherein the optoelectric receiver comprises a line camera configured to receive light directly, without the light having passed through a lens.

17. The device according to claim 16, wherein the at least one light source comprises a plurality of individual light sources, and a lens for pooling the light provided by the individual light sources to form a punctiform light source.

18. The device according to claim 16, further comprising: an additional measuring and/or recording region through which containers are moved in a conveyor, and at least one of an additional light-transmitting device configured for generating substantially parallel light through said additional measuring and/or recording region and an additional optoelectric receiver on one said additional measuring and/or recording region.

19. The device according to claim 16, wherein the at least one light-transmitting device comprises at least one of at least one substantially punctiform light source and at least one lens system for generating the parallel light, and at least one light source for delivering a light that has a modified spectrum.

20. The device according to claim 16, wherein the display screen has a transmission characteristic such that said display screen is only transparent to light incident from a pre-determined direction.

* * * * *